United States Patent
Hayashi et al.

(10) Patent No.: US 9,220,642 B2
(45) Date of Patent: Dec. 29, 2015

(54) ABSORBENT ARTICLE AND SANITARY NAPKIN WITH HEIGHTENED MIDDLE UNITS

(75) Inventors: Toshihisa Hayashi, Kagawa (JP); Tatsuya Tamura, Kagawa (JP); Nobuyuki Kato, Kagawa (JP)

(73) Assignee: Unicharm Corporation, Ehime (JP)

( * ) Notice: Subject to any disclaimer, the term of this patent is extended or adjusted under 35 U.S.C. 154(b) by 331 days.

(21) Appl. No.: 13/822,111

(22) PCT Filed: Sep. 9, 2011

(86) PCT No.: PCT/JP2011/005097
§ 371 (c)(1),
(2), (4) Date: May 31, 2013

(87) PCT Pub. No.: WO2012/032791
PCT Pub. Date: Mar. 15, 2012

(65) Prior Publication Data
US 2013/0274701 A1    Oct. 17, 2013

(30) Foreign Application Priority Data

Sep. 10, 2010 (JP) ................................. 2010-203267

(51) Int. Cl.
*A61F 13/15* (2006.01)
*A61F 13/20* (2006.01)
*A61F 13/475* (2006.01)
(Continued)

(52) U.S. Cl.
CPC ......... *A61F 13/4758* (2013.01); *A61F 13/4702* (2013.01); *A61F 13/4704* (2013.01); *A61F 13/476* (2013.01); *A61F 13/4753* (2013.01);
(Continued)

(58) Field of Classification Search
USPC ........................................ 604/385.28, 385.01
See application file for complete search history.

(56) References Cited

U.S. PATENT DOCUMENTS 6,326,525 B1 * 12/2001 Hamajima et al. ............. 604/378
6,506,961 B1 * 1/2003 Levy .............................. 604/380
(Continued)

FOREIGN PATENT DOCUMENTS

CN    101516303 A    8/2009
JP    11-033054      2/1999
(Continued)

OTHER PUBLICATIONS

Chinese Official Action and partial English translation from corresponding Chinese application No. 201180002002.9 dated Apr. 16, 2014 (6 pgs).

(Continued)

*Primary Examiner* — Michele M Kidwell
(74) *Attorney, Agent, or Firm* — Brinks Gilson & Lione (57) ABSTRACT

An absorbent article having a leakage preventing wall that includes a fixing unit and an erection unit. A heightened middle unit is disposed inside in the longitudinal direction more than a wing unit. Fold positions are provided in proximity to a base position of the wing unit. An end pan in the longitudinal direction of compression grooves are configured so as to be disposed outside in the longitudinal direction more than an end part in the longitudinal direction of the erection unit. The end part in the longitudinal direction of the erection unit and a site at which a dimension in the widthwise direction W is the greatest in the compression groove are disposed in proximity to the base position of the wing unit.

8 Claims, 4 Drawing Sheets

(51) Int. Cl.
 *A61F 13/47* (2006.01)
 *A61F 13/476* (2006.01)
 *A61F 13/515* (2006.01)
 *A61F 13/551* (2006.01)

(52) U.S. Cl.
 CPC .......... *A61F 13/4756* (2013.01); *A61F 13/515* (2013.01); *A61F 13/5514* (2013.01)

(56) References Cited

U.S. PATENT DOCUMENTS

| | | | |
|---|---|---|---|
| 7,048,726 B2 * | 5/2006 | Kusagawa et al. | 604/385.28 |
| 7,196,241 B2 * | 3/2007 | Kinoshita et al. | 604/380 |
| 7,438,708 B2 * | 10/2008 | Kashiwagi et al. | 604/385.31 |
| 7,641,642 B2 * | 1/2010 | Murai et al. | 604/385.28 |
| 8,075,541 B2 * | 12/2011 | Kameo et al. | 604/385.04 |
| 2004/0176734 A1 * | 9/2004 | Rasmussen et al. | 604/380 |

FOREIGN PATENT DOCUMENTS

| | | |
|---|---|---|
| JP | 2006-149413 | 6/2006 |
| JP | 2007-275491 | 10/2007 |
| JP | 2008-055110 | 3/2008 |
| JP | 2008-136739 | 6/2008 |
| JP | 2008-188181 | 8/2008 |
| JP | 2009-100846 | 5/2009 |
| JP | 2009-285240 | 12/2009 |
| JP | 2010-136917 | 6/2010 |

OTHER PUBLICATIONS

European Search Report from corresponding European application No. 11823270.1 dated Jun. 18, 2014 (7 pgs).

International Search Report from corresponding PCT application No. PCT/JP2011/005097 dated Dec. 13, 2011 (2 pgs).

Japanese Office Action and English translation from corresponding Japanese application No. 2010-203267 dated Sep. 16, 2014 (4 pgs).

Gulf Cooperation Council Examination Report from corresponding Gulf Cooperation Council application No. 2011/19251 dated Mar. 2, 2015 (5 pgs).

* cited by examiner

ABSORBENT ARTICLE AND SANITARY NAPKIN WITH HEIGHTENED MIDDLE UNITS

RELATED APPLICATION

This application is a 35 U.S.C. §371 national phase filing of International Patent Application No. PCT/JP2011/005097 filed Sep. 9, 2011, to which priority is claimed under 35 U.S.C. §120 and through which priority is claimed under 35 U.S.C. §119 to Japanese Patent Application No. 2010-203267, filed Sep. 10, 2010.

TECHNICAL FIELD

The present invention relates to an absorbent article, and in particular, to a sanitary napkin.

BACKGROUND ART

Conventionally, it is known that there is an absorbent article in which a heightened middle unit which is continuous in a longitudinal direction of an absorbent article in an absorber, and which is larger in thickness than a peripheral unit, is provided, and in which a wing unit extensive to each outside in a widthwise direction of the absorbent article is provided (for example, refer to Patent Document 1).

CITATION LIST

Patent Literature

[PTL 1] Japanese Unexamined Patent Application Publication No. 2009-100846

SUMMARY OF INVENTION

Technical Problem

However, the Applicant found the following problem associated with the above-mentioned absorbent article.

In such an absorbent article, a dimension in a longitudinal direction of a wing unit is smaller than a dimension in a longitudinal direction of the heightened middle unit, and since a fold position at the time of individual packing of the absorbent article is provided inside in the longitudinal direction of such a heightened middle unit, such a heightened middle unit is easily influenced by a folding kink which is exerted by the individual packing, and there has been a problem that, in a case where the wing unit is folded back and then is rolled up at a crotch of underwear, the heightened middle unit is not restored to its flat state.

Therefore, the present invention has been made in view of the problem described above, and it is an object of the present invention to provide an absorbent article and a sanitary napkin which are capable of easily restoring a heightened middle unit in an absorber to its flat state, in a case where a wing unit is folded back and then is rolled up at a crotch of underwear.

Solution to Problem

The first feature of the present invention is summarized in that an absorbent article having a topsheet, a backsheet, and an absorber which is disposed between the topsheet and the backsheet, the absorbent article being folded and individually packed along at least a widthwise direction, said absorbent article comprising:

a wing unit which is extensive at each outside in the widthwise direction of the absorbent article;
a leakage preventing wall which has an elastic member arranged along a longitudinal direction of the absorbent article and which, when the absorbent article is worn, is configured so as to be erected from a non-skin contact surface side of the absorbent article toward a skin contact surface side of the absorbent article; and at least one annular compression groove which is provided at the skin contact surface side of the absorbent article, wherein: the absorber has a heightened middle unit which is larger in thickness than a peripheral unit; the leakage preventing wall has: a fixing unit which is fixed at the skin contact surface side of the absorbent article at an end part in the longitudinal direction in order to restrain erection of the leakage preventing wall; and an erection unit which is configured so that the leakage preventing wall is erected inside in the longitudinal direction more than the fixing unit; the heightened middle unit is disposed inside in the longitudinal direction more than the wing unit; a fold position at the time of individual packing of the absorbent article is provided in proximity to a base portion of the wing unit; an end part in the longitudinal direction of the compression groove is configured so as to be disposed outside in the longitudinal direction more than an end part in the longitudinal direction of the erection unit; and the end part in the longitudinal direction of the erection unit and a site at which a dimension in the widthwise direction is the greatest in the compression groove are disposed in proximity to the base portion of the wing unit.

The second feature of the present invention is summarized in that a sanitary napkin including a main unit which has a topsheet, a backsheet, and an absorber which is disposed between the topsheet and the backsheet, the sanitary napkin being folded along at least in a widthwise direction and individually packed, said sanitary napkin comprising: a wing unit which is extensive to each outside in a widthwise direction of the absorbent article; a leakage preventing wall which has an elastic member arranged along a longitudinal direction of the absorbent article and which, when the absorbent article is worn, is configured so as to be erected from a non-skin contact surface side of the absorbent article toward a skin contact surface side of the absorbent article; a compression groove including a first compression groove and a second compression groove, the first compression groove which is formed in an annular shape and is provided at the skin contact surface side of the absorbent article; and the second compression which is formed in an annular shape and disposed inside of the first compression groove at the skin contact surface side of the absorbent article, wherein: the absorber has a heightened middle unit which is larger in thickness than a peripheral unit; the leakage preventing wall has: a fixing unit which is fixed to the skin contact surface side of the absorbent article at an end part in the longitudinal direction in order to restrain erection of the leakage preventing wall; and an erection unit which is configured so that the leakage preventing wall can be erected inside in the longitudinal direction more than the fixing unit; the heightened middle unit is disposed inside in the longitudinal direction more than the wing unit; a fold position at a time of individual packing of the absorbent article is provided in proximity to a base portion of the wing unit; an end part in the longitudinal direction of the compression groove is configured so as to be disposed outside in the longitudinal direction more than the base portion of the wing unit; an end part in the longitudinal direction of the erection unit and a site at which a dimension in the widthwise direction is the greatest in the compression groove are configured so as to be disposed in proximity to the base portion of the wing unit; a reinforcing member is mounted to the wing unit; a dimension of the reinforcing member is configured so as to be greater than a dimension of the wing unit in the longitudinal direction; the leakage preventing wall is bonded with the topsheet by means of a heat seal at the erection unit; the heat seal is bent toward an inside of the absorbent article at each end part in the longitudinal direction; and an end part in the longitudinal direction of the second compression groove is configured so as to be disposed in proximity to the site at which the dimension in the widthwise direction is the greatest in the first compression groove.

Advantageous Effects of Invention

As has been described above, according to the present invention, there can be provided an absorbent article and a sanitary napkin which are capable of easily restoring a heightened middle unit in an absorber to its flat state, in a case where a wing unit is folded back and then is roll up at a crotch of underwear.

DESCRIPTION OF EMBODIMENTS

First Embodiment of the Present Invention

An absorbent article 1 according to a first embodiment of the present invention will be described with reference to FIG. 1 to FIG. 4. For example, the absorbent article 1 according to the embodiment is a paper diaper, an incontinent pad, a sanitary napkin or the like. Hereinafter, the absorbent article 1 according to the embodiment will be described by way of example of sanitary napkin.

Figure 1:
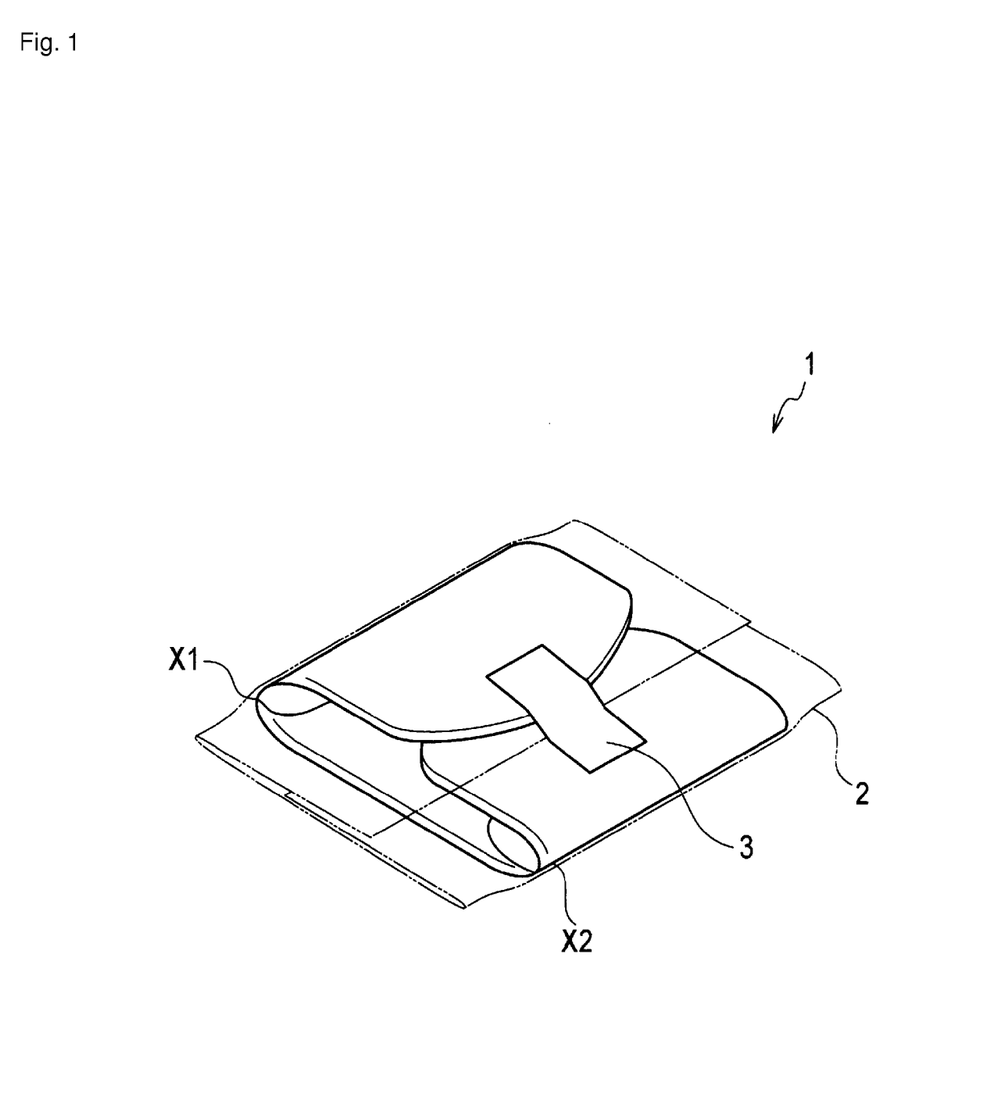
FIG. 1 is a view showing a state in which an absorbent article according to a first embodiment of the present invention is individually packed.

As shown in FIG. 1, such an absorbent article 1 is folded into three or four sections along a widthwise direction W, and is configured so as to be individually packed by means of a packing sheet 2 made of a nonwoven cloth, a plastic resin film or the like.

In a state in which such an absorbent article 1 is individually packed, the packing sheet 2 is engagingly locked by means of an engagingly locking member 3.

Figure 2:
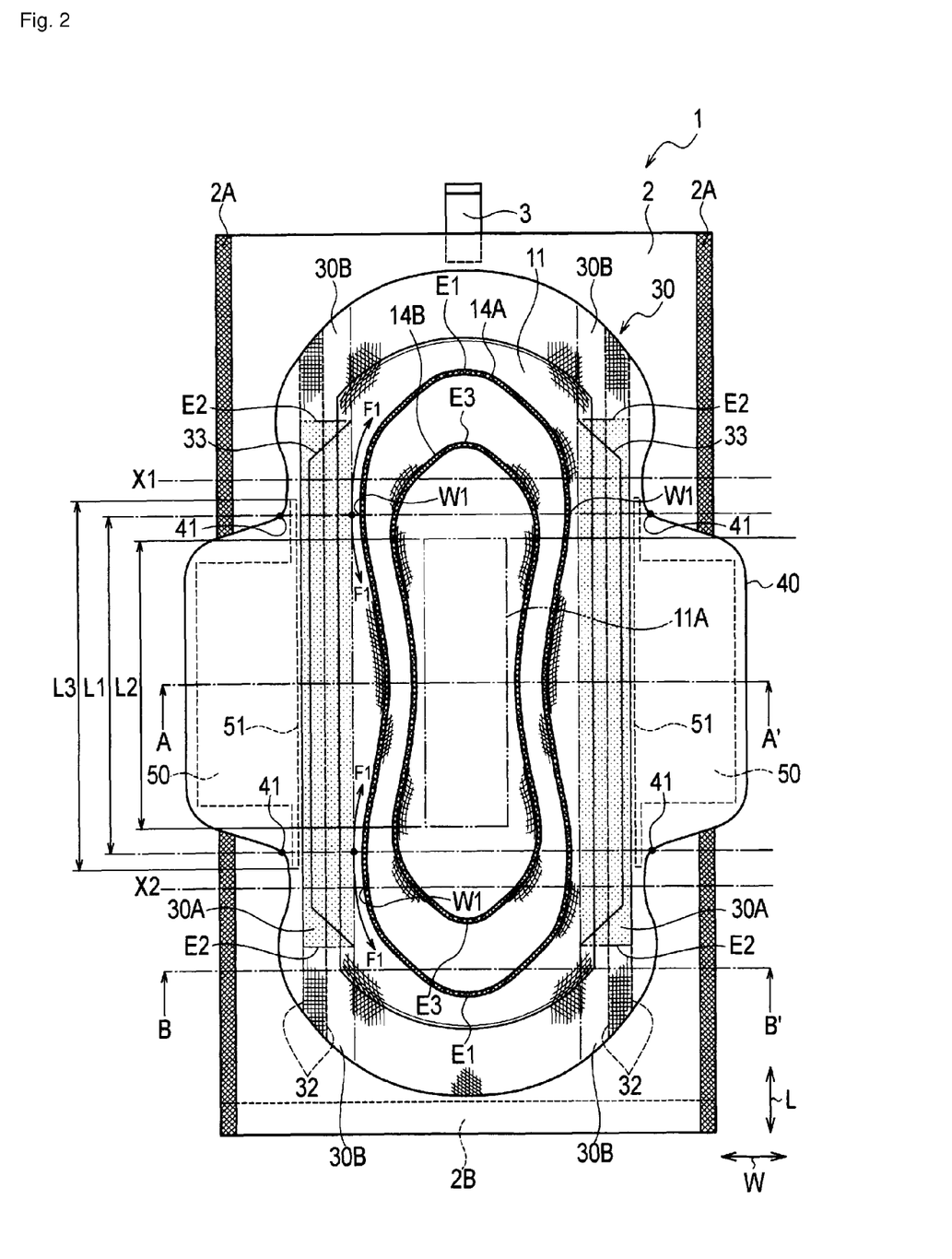
FIG. 2 is a plan view of the absorbent article according to the first embodiment of the present invention when it is seen from a skin contact surface side thereof.

Herein, the absorbent article 1 according to the embodiment, as shown in FIG. 1 and FIG. 2, is configured so as to be folded into three sections by means of fold positions X1, X2 in the widthwise direction W.

In addition, processing such as a thermal emboss may be applied to a side unit 2A of the packing sheet 2. Further, a perforation unit 2B of the packing sheet 2 may be bonded by means of an adhesive or the like.

As such a nonwoven cloth, there is employed: a span lace nonwoven cloth; an air through nonwoven cloth; a span bond nonwoven cloth; or a point bond nonwoven cloth or the like, which is comprised of a cellulose fiber such as rayon or a synthetic resin fiber.

Furthermore, as such a plastic resin film, there is employed a film or the like obtained by film-forming and thin-filming polyethylene (PE), polypropylene (PP), or polyester (PET which is a thermoplastic resin. For such a film, an inorganic filler made of titanium oxide, calcium carbonate or the like may be mixed and clouded in a range of 0.5 to 10 mass % as required.

Figure 3:
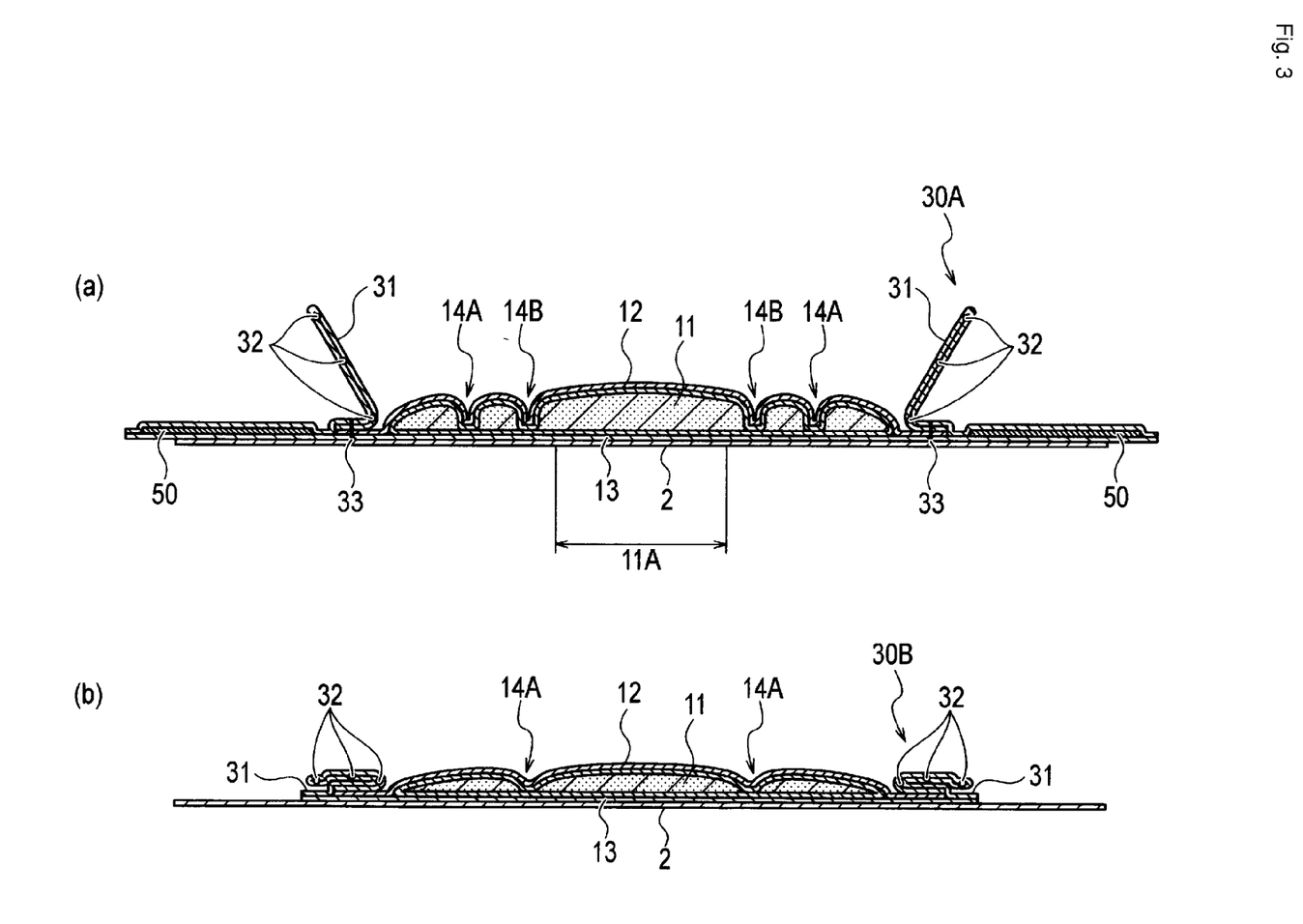
FIG. 3 is a sectional view taken along the line A-A', and a sectional view taken along the line B-B', of the absorbent article according to the first embodiment of the present invention.

Hereinafter, FIG. 2 shows a plan view of the absorbent article 1 according to the embodiment when it is seen from the skin contact surface side thereof; FIG. 3 (*a*) shows a sectional view taken along the line A-A' of the absorbent article 1 according to the embodiment; and FIG. 3 (*b*) shows a sectional view taken along the line B-B of the absorbent article 1 according to the embodiment.

As shown in FIG. 2, the absorbent article 1 is formed in a longitudinal manner. For example, the dimension in the longitudinal direction of the absorbent article 1 is 100 mm to 500 mm and is preferably 210 mm to 290 mm.

As shown in FIG. 3, the absorbent article 1 has: a liquid permeable topsheet 12 which is provided at the skin contact surface side; a liquid impermeable backsheet 13 which is provided at a non-skin contact surface side; and an absorber 11 which is disposed between the topsheet 12 and the backsheet 13. Incidentally, the absorbent article 1 can be manufactured by the conventional manufacturing method, for example, the manufacturing method described in Japanese Unexamined Patent Application Publication No. H11-033054.

Herein, the topsheet 12 is disposed at a body side of a wearer while in use, and in particular, is brought into contact with an excretion portion of the wearer. An entire face of the topsheet 12 may be liquid-permeable or a part of the topsheet 12 may be liquid-permeable. In addition, the topsheet 12 may be comprised of one sheet member or may be comprised of a plurality of sheet members which are bonded with each other.

In the absorbent article 1 according to the embodiment, a liquid permeable region is provided in a central region in a widthwise direction W of the topsheet 12, and an end part in the widthwise direction W of the topsheet 12 is covered with a liquid impermeable leakage preventing sheet (side sheet) 31.

As a material used for the topsheet 12, there can be used a material, all or part of which is liquid-permeable and which does not impart a stimulus to a wearer's skin.

For example, the material used for the topsheet 12, there can be exemplified: a plastic resin film on which a number of liquid permeable pores are formed; liquid permeable nonwoven cloth or woven cloth; or the like. These materials are used solely or are used in combination.

As a resin film, there is employed: a film obtained by film-forming or thin-filming polyethylene (PE), polypropylene (PP), or polyester (PET) or the like which is a thermoplastic resin.

For example, there can be employed a perforated plastic resin obtained by extruding a low density polyethylene (LDPE) in a sheet shape; thin-filming the extruded polyethylene; and then adjusting the thin-filmed polyethylene to 10 to 30 g/m$^2$. For such a film, an inorganic filler made of titanium oxide, calcium carbonate or the like may be mixed and clouded in a range of 0.5 to 10 mass %, as required.

As a nonwoven cloth, there is employed: a span lace nonwoven cloth; an air through nonwoven cloth; a span bond nonwoven cloth; a point bond nonwoven cloth or the like which is comprised of a cellulose fiber such as rayon or a synthetic resin fiber.

For example, there can be employed an air through nonwoven cloth in which: a fiber whose large-diameter hydrophobic fiber is mixed at a rate of 30 to 50 mass % and whose small-diameter hydrophobic fiber is mixed at a rate of 50 to 70 mass % is disintegrated and then is adjusted in a range of 20 g/m² or less; and thereafter, the fibers are fused by means of hot air; and a fiber length whose thickness is adjusted in a range of 0.2 mm or more and 2 mm or less is formed from a range of 1 to 50 mm.

In addition, as the backsheet 13, there can be used a material which is capable of preventing a liquid, which is absorbed by an absorber 11, from leaking to the outside of the absorbent article 1.

Such a material, there is exemplified a liquid impermeable polyethylene, polypropylene, polyethylene terephthalate, polyvinyl alcohol, polylactate, polybutyl succinate, a nonwoven cloth, paper, or a laminate material thereof.

In addition, such a material, there may be employed an air ventilation film which is obtained by filling with an inorganic filler and then applying rolling treatment. For example, as such a material, there can be employed a film which is adjusted in a range of 15 to 30 g/m², the film consisting essentially of a low density polyethylene resin.

While a material for the absorber 11 is not limited in particular as long as it is capable of absorbing and retaining a liquid, it is preferable that the material is bulky, is hardly deformed, and is less in chemical stimulate.

As a material used for the absorber 11, there can be employed: pulp, chemical pulp, rayon, rayon acetate, natural cotton, polymeric absorptive polymer, fibrous polymeric absorber, or synthetic resin solely or a mixture thereof.

For example, there is used the one obtained by adjusting the pulp crushed as the material used for the absorber 11 to 50 to 600 g/m²; mixing polymeric absorptive polymer in a range of 0.1 to 10 mass %; and then, pressing a mixture by means of emboss processing with the mixture being covered with tissue.

In addition, the absorbent article 1 has one pair of wing units 40 which are formed so as to be extensive to both outsides in the widthwise direction W. Herein, a wearer is allowed to roll the wing unit 40 up at underwear, and then, fix the absorbent article 1 to the underwear at the time of wearing the absorbent article 1 on the underwear.

An adhesive agent is applied to a non-skin contact surface side of the backsheet 13, and the absorbent article 1 is fixed to the underwear by means of such an adhesive agent.

In addition, an adhesive agent is applied to the side of the backsheet 13 of the wing unit 40, and then, the wing unit 40 is folded back and adhered to a non-skin contact surface side of the underwear by means of such an adhesive agent, whereby the absorbent article 1 is fixed to the underwear.

As such an adhesive agent, there can be used a material which is capable of fixing the absorbent article 1 and underwear to each other. As such an adhesive agent, for example, there can be employed: a pressure sensitive adhesive agent consisting essentially of a synthetic rubber such as a styrene-ethylene butadiene-styrene block copolymer (SEBS), a styrene-butadiene-styrene copolymer (SBS), styrene-isoprene-styrene block copolymer (SIS) or the like; or alternatively, a thermo-sensitive adhesive agent consisting essentially of a synthetic rubber such as EVA. As such an adhesive agent, there may be employed a mechanical fastener or a styrene-based slip preventing agent.

In such an absorbent article 1, a leakage preventing wall 30 is provided along the longitudinal direction L on each side in the widthwise direction W. The leakage preventing wall 30 is configured so as to be erected from the non-skin contact surface side of the absorbent article 1 toward the skin contact surface side of the absorbent article 1 when the absorbent article 1 is worn.

Such a leakage preventing wall 30 is comprised of: a leakage preventing sheet 31 which is folded on a hollow; and an elastic member 32 which is arranged along the longitudinal direction L in an expanded state between the leakage preventing sheets 31.

Herein, the leakage preventing sheet 31 is a liquid impermeable sheet, and as the elastic member 32, there may be employed the one consisting of natural rubber, synthetic rubber or the like. In addition, one or more elastic members 32 may be used.

As shown in FIG. 2, in the absorbent article 1 according to the embodiment, annular compression grooves 14A and 14B which are configured so as to compress a site from the topsheet 12 to the absorber 11 are provided at the skin contact surface side.

The leakage preventing wall 30, as shown in FIG. 2 and FIG. 3, has: a fixing unit 30B which is fixed to the skin contact surface side of the absorbent article 1 at an end part in the longitudinal direction L in order to restrain erection of the leakage preventing wall 30; and an erection unit 30A which is configured so that the leakage preventing wall 30 can be erected inside in the longitudinal direction L more than the fixing unit 30B. That is, the erection unit 30A in the leakage preventing wall 30 is a region which effectively functions as the leakage preventing wall 30.

Herein, the leakage preventing wall 30 is bonded with the topsheet 12 by means of a heat seal 33 at the erection unit 30A. The heat seal 33 is bent toward the inside of the absorbent article 1 at each end part in the longitudinal direction L.

Figure 4:
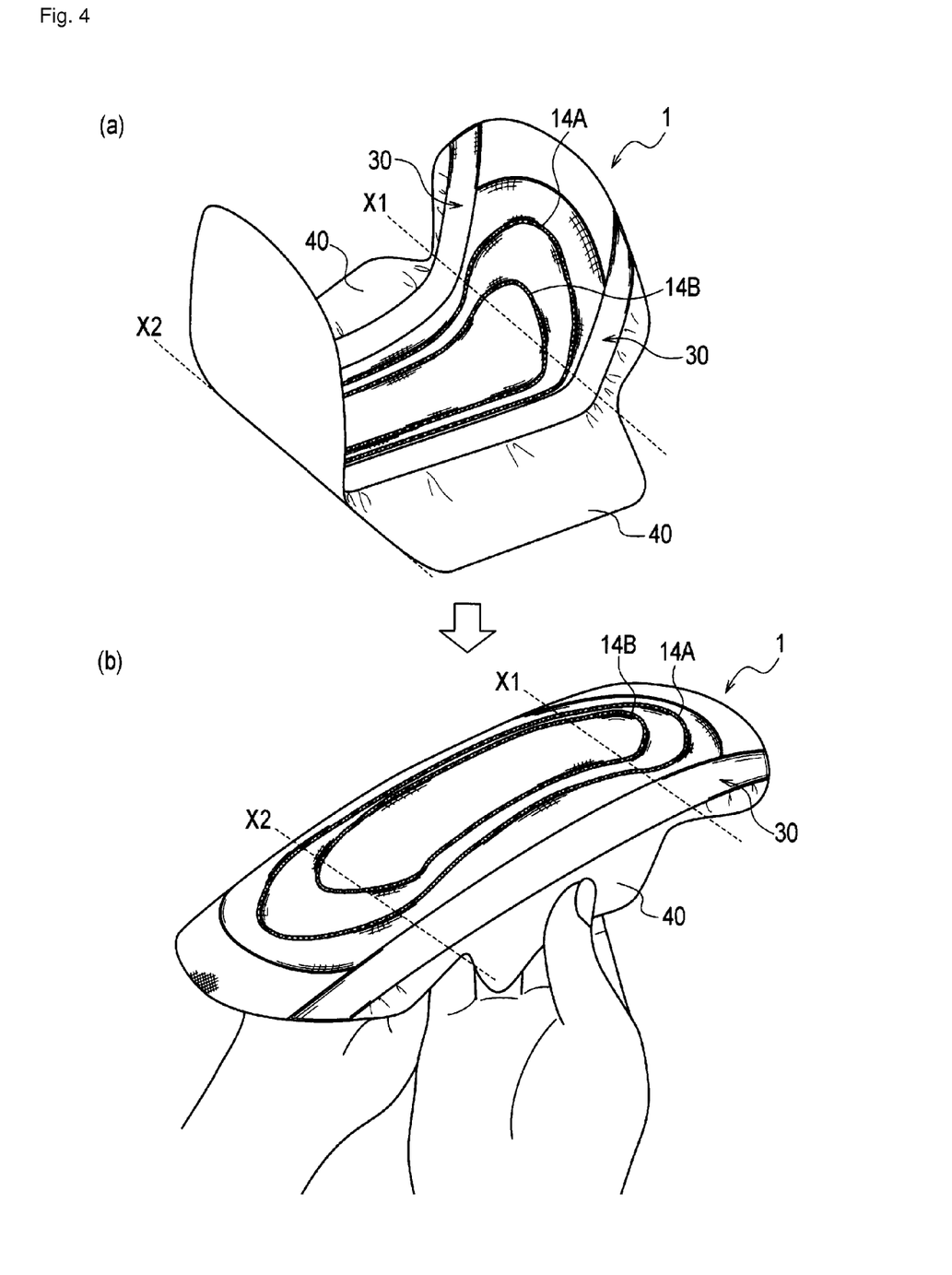
FIG. 4 is a view for explaining functions and advantageous effects in the absorbent article according to the first embodiment of the present invention.

According to such a structure, in a case where a wing unit 40 is rolled up at a crotch of underwear, as shown in FIG. 4 (b), in the absorbent article 1, a side edge part of the heat seal 33 is folded along the longitudinal direction L, and since a force of folding downward along the widthwise direction W is transmitted to a portion at which the heat seal 33 is bent, the absorbent article 1 can be mounted on the underwear in a state in which the leakage preventing wall 30 is expanded.

Further, the side edge part of the heat seal 33 is folded along the longitudinal direction L, and the erection unit 30A of the leakage preventing wall 30 is lifted, whereby erection of the leakage preventing wall 30 is accelerated, thus making it possible to prevent a side leakage of bodily fluids.

The absorber 11, as shown in FIG. 2 and FIG. 3, has a heightened middle unit 11A which is extensive in the longitudinal direction L and is larger in thickness than a peripheral unit.

Herein, as shown in FIG. 2, annular compression grooves 14A and 14B are provided at the periphery of such a heightened middle unit 11A. Specifically, the compression groove 14B is arranged inside of the compression groove 14A.

The compression grooves 14A and 14B may be continuously formed in an annular shape or may be formed intermittently in an annular shape. However, it should be kept in mind that a force of pressing the absorbent article 1 towards underwear is transmitted more easily in a case where the compression grooves 14A and 14B are formed continuously in an annular shape.

An end part E3 in the longitudinal direction L of the compression groove 14B is configured so as to be arranged in proximity to a site W1 at which a dimension in the widthwise direction W is the greatest in the compression groove 14A. For example, a distance between the end part E3 in the longitudinal direction L of the compression groove 14B and the site W1 at which the dimension in the widthwise direction W is the greatest in the compression groove 14A is within a range of 0 to 20 mm.

According to such a structure, a force F1 pressing the absorbent article 1 towards underwear, which is generated in a case where the wing unit 40 is rolled up at a crotch of the underwear, acts on the site W1 at which the dimension in the widthwise direction W is the greatest in the compression groove 14A and the end part E3 in the longitudinal direction L of the compression groove 14B.

Such a force F1 is then transmitted to the end part E1 in the longitudinal direction L of the compression groove 1 along the compression groove 14A, with such a site W1 being a start point in the compression groove 14A.

As a result, since such a force F1 acts along the widthwise direction W at the end part E1 which is close to an end part in the longitudinal direction L of the absorbent article 1 and at the end part E3 which is disposed inside in the longitudinal direction L more than the end part E1, the absorbent article 1 can be securely fixed to the underwear, and can be used in a stable manner for a long period of time without being twisted.

In addition, as shown in FIG. 2, the heightened middle unit 11A is disposed inside in the longitudinal direction L more than the wing unit 40. Specifically, a dimension L1 in the longitudinal direction L of the wing unit 40 is configured to be greater than a dimension L2 in the longitudinal direction L of the heightened middle unit 11A.

Further, as shown in FIG. 2, fold positions X1, X2 at the time of individual packing of the absorbent article 1 are provided in the vicinity of a base position 41 of the wing unit 40. For example, a distance between the base position 41 of the wing unit 40 and each of the fold positions X1, X2 is within a range of 0 to 10 mm.

According to such a structure, the heightened middle unit 11A is disposed inside in the longitudinal direction L more than the wing unit 40, and since the fold position at the time of individual packing of the absorbent article is disposed in proximity to the base portion 1 of the wing unit 40, such a heightened middle unit 11A is hardly influenced by the folding kink that is exerted by individual packing, and as shown in FIG. 4 (a) and FIG. 4 (b), in a case where the wing unit 40 is folded back and is rolled up at a crotch of underwear, the fold positions X1, X2 of the absorbent article 1 are easily restored in a flat state.

In addition, as shown in FIG. 2, the end part E1 in the longitudinal direction L of the compression groove 14A is configured so as to be disposed outside in the longitudinal direction L more than the end part E2 in the longitudinal direction L of the erection unit 30A.

Further, as shown in FIG. 2, the end part E2 in the longitudinal direction L of the erection unit 30A is configured so as to be disposed in proximity to the site W1 at which the dimension in the widthwise direction W is the greatest in the compression groove 14A. For example, a distance between the end part E2 in the longitudinal direction L of the erection unit 30A and the site W1 at which the dimension in the widthwise direction W is the greatest in the compression groove 14A is within a range of 0 to 20 mm.

According to such a structure, since a force of pressing the absorbent article 1 in the direction of underwear acts on the erection unit 30A of the leakage preventing wall 30, the absorbent article 1 can be securely fixed to the underwear, and then, the absorbent article 1 can be used in a stable manner for a long period of time by means of a stress of the leakage preventing wall 30 without being twisted.

In addition, as shown in FIG. 2, the end part E1 in the longitudinal direction L of the compression groove 14A is configured so as to be disposed outside in the longitudinal direction L more than the base position 41 of the wing unit 40. Preferably, the end part E3 in the longitudinal direction L of the compression groove 14B is configured so as to be disposed outside in the longitudinal direction L more than the site W1 at which the dimension in the widthwise direction W is the greatest in the compression groove 14A.

Further, as shown in FIG. 2, the base position 41 of the wing unit 40 is configured so as to be disposed in proximity to the site W1 at which the dimension in the widthwise direction W is the greatest in the compression groove 14A. Preferably, the base position 41 of the wing unit 40 is configured so as to be disposed in the same position in the longitudinal direction L as the site W1 at which the dimension in the widthwise direction W is the greatest in the compression groove 14A.

According to such a structure, the force F1 of pressing the absorbent article 1 in the direction of underwear, which is generated in a case where the wing unit 40 is rolled up at a crotch of the underwear, is transmitted along the compression groove 14A while the site W1 at which the dimension in the widthwise direction W is the greatest in the compression groove 14A is defined as a start point.

Therefore, said force F1, along the longitudinal direction L, acts more to the inside of the absorbent article than the base position 41 of the wing unit 40, and along the widthwise direction W acts more to the outside in the absorbent article than the base position 41 of the wing unit 40.

As a result, the absorbent article 1 can be securely fixed to the underwear, and can be used in a stable manner for a long period of time without being twisted.

A reinforcing member 50 is mounted to the wing unit 40, as shown in FIG. 2 and FIG. 3. Herein, an inside end part 51 in the widthwise direction W of the reinforcing member 50 is configured so as to be disposed inside in the widthwise direction W more than the base position 41 of the wing unit 40.

In addition, as shown in FIG. 2, in the longitudinal direction L, a dimension L3 of the reinforcing member 50 may be configured so as to be greater than the dimension L1 of the wing unit 40.

The shape of the reinforcing member 50 may be the shape as shown in FIG. 2 or may be another shape (for example, a rectangular shape).

According to such a structure, in a case where the wing unit 40 is rolled up at a crotch of underwear, since the wing unit 40 is folded while an inside end part 51 in the widthwise direction W of the reinforcing member 50 is defined as a folding start point, that is, since the wing unit 40 is folded inside in the widthwise direction more than the base position 41 of the wing unit 40 and outside in the longitudinal direction W more than the base position 41 of the wing unit 40, the entirety of the absorbent article 1 can be securely fixed to the underwear.

While the present invention has been described in detail hereinbefore by way of the foregoing embodiment, it is apparent to one skilled in the art that the present invention is not limited to the embodiment described in the present specification. The present invention can be carried out as aspects of alteration and modification without deviating from the gist and scope of the present invention which are defined by the claims. Therefore, the description of the present specification is intended for illustrative explanation and does not have any limitative meaning to the present invention.

The present invention is also defined by way of the following non-limiting features which are not specific to the detailed embodiments described above:

(a) An absorbent article in which the leakage preventing wall is bonded with the topsheet by means of a heat seal which is continuously disposed along the longitudinal direction at the erection unit; and the heat seal is angled, at each end part in the longitudinal direction, inwards in the planar dimension towards the inside of the absorbent article.

(b) An absorbent article in which a reinforcing member is mounted to the wing unit; and an inside end part in the widthwise direction of the reinforcing member is configured so as to be disposed more towards the inside of the absorbent article in the widthwise direction than a base portion of the wing unit.

(c) An absorbent article in which the dimension of the reinforcing member in the longitudinal direction is greater than the dimension of the wing unit in the longitudinal direction.

(d) An absorbent article in which a first compression groove is formed in an annular shape;
a second compression groove is formed in an annular shape and is disposed inside of the first compression groove; and an end part in the longitudinal direction of the second compression groove is configured so as to be disposed in proximity to a site at which the dimension of the area defined by the first compression groove in the widthwise direction is greatest.

The invention claimed is:

1. An absorbent article having a top sheet, a backsheet, and an absorber which is disposed between the top sheet and the backsheet, the absorbent article being folded and individually packed along at least a widthwise direction, said absorbent article comprising:
   a wing unit which is extensive at each outside in the widthwise direction of the absorbent article;
   a leakage preventing wall which has an elastic member arranged along a longitudinal direction of the absorbent article and which, when the absorbent article is worn, is configured so as to be erected from a non-skin contact surface side of the absorbent article toward a skin contact surface side of the absorbent article; and
   at least one annular compression groove which is provided at the skin contact surface side of the absorbent article, wherein:
   the absorber has a heightened middle unit which is larger in thickness than a peripheral unit; the leakage preventing wall has: a fixing unit which is fixed at the skin contact surface side of the absorbent article at an end part in the longitudinal direction in order to restrain erection of the leakage preventing wall; and an erection unit which is configured so that the leakage preventing wall is erected inside in the longitudinal direction more than the fixing unit;
   the heightened middle unit is disposed inside in the longitudinal direction more than the wing unit;
   a fold position is provided in proximity to a base portion of the wing unit;
   an end part in the longitudinal direction of the compression groove is configured so as to be disposed outside in the longitudinal direction more than an end part in the longitudinal direction of the erection unit;
   the end part in the longitudinal direction of the erection unit and a site at which a dimension in the widthwise direction is the greatest in the compression groove are disposed in proximity to the base portion of the wing unit;
   the leakage preventing wall is bonded with the to sheet by means of a heat seal which is continuously disposed along the longitudinal direction at the erection unit;
   the heat seal is curved toward an inside of the absorbent article at each end part in the longitudinal direction at a plan view of the absorbent article;
   the compression groove has: a first compression groove which is formed in an annular shape; and a second compression groove which is formed in an annular shape and which is disposed inside of the first compression groove; and
   the curved portion of the heat seal extends toward an end part in the longitudinal direction of the first compression groove in a position in the longitudinal direction close to an end part in the longitudinal direction of the second compression groove.

2. The absorbent article according to claim 1, wherein:
   a reinforcing member is mounted to the wing unit; and
   an inside end part in the widthwise direction of the reinforcing member is configured so as to be disposed inside in the widthwise direction more than the base portion of the wing portion.

3. The absorbent article according to claim 2, wherein:
   a dimension of the reinforcing member is configured so as to be greater than a dimension of the wing unit in the longitudinal direction.

4. The absorbent article according to claim 1, wherein:
   an end part in the longitudinal direction of the second compression groove is configured so as to be disposed in proximity to a site at which a dimension in the widthwise direction is the greatest in the first compression groove.

5. A sanitary napkin including a main unit which has a top sheet, a backsheet, and an absorber which is disposed between the topsheet and the backsheet, the sanitary napkin being folded along at least in a widthwise direction and individually packed, said sanitary napkin comprising:
   a wing unit which is extensive to each outside in a widthwise direction of the absorbent article;
   a leakage preventing wall which has an elastic member arranged along a longitudinal direction of the absorbent article and which, when the absorbent article is worn, is configured so as to be erected from a non-skin contact surface side of the absorbent article toward a skin contact surface side of the absorbent article;
   a compression groove including a first compression groove and a second compression groove, the first compression groove which is formed in an annular shape and is provided at the skin contact surface side of the absorbent article; and the second compression which is formed in an annular shape and disposed inside of the first compression groove at the skin contact surface side of the absorbent article, wherein:
   the absorber has a heightened middle unit which is larger in thickness than a peripheral unit;
   the leakage preventing wall has: a fixing unit which is fixed to the skin contact surface side of the absorbent article at an end part in the longitudinal direction in order to restrain erection of the leakage preventing wall; and an erection unit which is configured so that the leakage preventing wall can be erected inside in the longitudinal direction more than the fixing unit;
   the heightened middle unit is disposed inside in the longitudinal direction more than the wing unit;
   a fold position at a time of individual packing of the absorbent article is provided in proximity to a base portion of the wing unit;

an end part in the longitudinal direction of the compression groove is configured so as to be disposed outside in the longitudinal direction more than the base portion of the wing unit;

an end part in the longitudinal direction of the erection unit and a site at which a dimension in the widthwise direction is the greatest in the compression groove are configured so as to be disposed in proximity to the base portion of the wing unit;

a reinforcing member is mounted to the wing unit;

a dimension of the reinforcing member is configured so as to be greater than a dimension of the wing unit in the longitudinal direction;

the leakage preventing wall is bonded with the topsheet by means of a heat seal at the erection unit;

the heat seal is curved toward an inside of the absorbent article at each end part in the longitudinal direction at a plan view of the sanitary napkin;

an end part in the longitudinal direction of the second compression groove is configured so as to be disposed in proximity to the site at which the dimension in the widthwise direction is the greatest in the first compression groove the curved portion of the heat seal extends toward an end part in the longitudinal direction of the first compression groove in a position in the longitudinal direction close to an end part in the longitudinal direction of the second compression groove.

6. The absorbent article according to claim 1, wherein: a reinforcing member is mounted to the wing unit; and an inside end part in the widthwise direction of the reinforcing member is configured so as to be disposed inside in the widthwise direction more than the base portion of the wing portion.

7. The absorbent article according to claim 6, wherein:
a dimension of the reinforcing member is configured so as to be greater than a dimension of the wing unit in the longitudinal direction.

8. The absorbent article according to claim 1, wherein: the compression groove has: a first compression groove which is formed in an annular shape; and a second compression groove which is formed in an annular shape and which is disposed inside of the first compression groove; and an end part in the longitudinal direction of the second compression groove is configured so as to be disposed in proximity to a site at which a dimension in the widthwise direction is the greatest in the first compression groove.

* * * * *